United States Patent
Hill

(10) Patent No.: US 11,212,201 B2
(45) Date of Patent: Dec. 28, 2021

(54) SYSTEM AND METHOD FOR MONITORING HEALTH STATUS BASED ON HOME INTERNET TRAFFIC PATTERNS

(71) Applicant: KONINKLIJKE PHILIPS N.V., Eindhoven (NL)

(72) Inventor: Peter Douglas Hill, Murrysville, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 17/111,678

(22) Filed: Dec. 4, 2020

(65) Prior Publication Data

US 2021/0176147 A1     Jun. 10, 2021

Related U.S. Application Data

(60) Provisional application No. 62/945,447, filed on Dec. 9, 2019.

(51) Int. Cl.
  *H04L 12/00* (2006.01)
  *H04L 12/26* (2006.01)
  *H04L 29/12* (2006.01)
  *H04L 29/08* (2006.01)

(52) U.S. Cl.
  CPC .......... *H04L 43/062* (2013.01); *H04L 43/022* (2013.01); *H04L 43/04* (2013.01); *H04L 43/12* (2013.01); *H04L 61/6022* (2013.01); *H04L 69/326* (2013.01)

(58) Field of Classification Search
  CPC ............. H04L 43/0858; H04L 61/2015; H04L 41/0893; H04L 49/351; H04W 8/26
  USPC .................................................. 709/223–226
  See application file for complete search history.

(56) References Cited

U.S. PATENT DOCUMENTS

| | | | | |
|---|---|---|---|---|
| 6,480,471 | B1 * | 11/2002 | VanZante | H04L 29/06 370/252 |
| 7,020,082 | B2 * | 3/2006 | Bhagavath | H04L 43/00 370/230 |
| 7,443,803 | B2 * | 10/2008 | Su | H04L 41/142 370/252 |
| 7,554,959 | B1 * | 6/2009 | Dowling | H04L 49/351 370/338 |
| 7,911,975 | B2 * | 3/2011 | Droz | H04L 43/028 370/254 |

(Continued)

OTHER PUBLICATIONS

International Search Report and Written Opinion, International Application No. PCT/EP2020/083273, dated Feb. 19, 2021.

*Primary Examiner* — Frantz Coby

(57) ABSTRACT

A health status monitoring method includes: (a) analyzing transport layer data for a dwelling to identify a plurality of occupant specific transport layer data items based on MAC address mapping, (b) establishing an Internet traffic pattern for the occupant for a period of time based on the identified plurality of occupant specific transport layer data items, (c) comparing the established Internet traffic pattern to a predetermined baseline Internet traffic pattern for the occupant and identifying a deviation from the predetermined baseline Internet traffic pattern based on the comparison, and (d) determining that a change in the health status is possible for the occupant based on the identifying of the deviation.

17 Claims, 10 Drawing Sheets

(56) References Cited

U.S. PATENT DOCUMENTS

| | | | | |
|---|---|---|---|---|
| 8,190,734 | B2* | 5/2012 | Cooper | G06F 21/554 709/224 |
| 8,307,068 | B2* | 11/2012 | Schuler | G06F 11/3006 709/224 |
| 9,084,108 | B2* | 7/2015 | Zhu | H04W 8/26 |
| 9,307,418 | B2* | 4/2016 | Papakostas | H04W 24/00 |
| 9,584,522 | B2* | 2/2017 | John | H04L 67/22 |
| 9,692,679 | B2* | 6/2017 | Shah | H04L 43/0858 |
| 10,291,473 | B2* | 5/2019 | Joshi | H04L 41/0893 |
| 10,693,982 | B1* | 6/2020 | Alpert | H04L 61/2015 |
| 2004/0073533 | A1* | 4/2004 | Mynarski | G06F 16/958 |
| 2006/0092841 | A1* | 5/2006 | Lloyd | H04L 47/10 370/231 |
| 2010/0313229 | A1* | 12/2010 | Martini | H04N 5/765 725/105 |
| 2013/0276054 | A1* | 10/2013 | Martini | H04L 63/1408 726/1 |
| 2016/0036843 | A1* | 2/2016 | Oh | H04L 63/1425 726/23 |
| 2017/0286624 | A1* | 10/2017 | Xu | G16H 50/50 |
| 2018/0212989 | A1* | 7/2018 | Mavani | H04L 63/1433 |

\* cited by examiner

| NO. | TIME | SOURCE | DESTINATION | PROTOCOL |
|---|---|---|---|---|
| | | LAPTOP LAN IP ADDRESS | IOT LAN IP ADDRESS | |
| 3383 | 76.796622 | 192.168.1.33 | 192.168.1.155 | TCP |
| 3384 | 76.796681 | 192.168.1.155 | 192.168.1.33 | TCP |
| 3385 | 76.796752 | 192.168.1.33 | 192.168.1.155 | TCP |
| 3386 | 76.796814 | 192.168.1.155 | 192.168.1.33 | TCP |
| 3387 | 76.797469 | 192.168.1.155 | 192.168.1.33 | TCP |
| 3388 | 76.797635 | 192.168.1.155 | 192.168.1.33 | TCP |
| 3389 | 76.797729 | 192.168.1.33 | 192.168.1.155 | TCP |
| 3390 | 76.797730 | 192.168.1.33 | 192.168.1.155 | TCP |
| 3391 | 76.797782 | 192.168.1.155 | 192.168.1.33 | TCP |
| 3392 | 76.797841 | 192.168.1.33 | 192.168.1.155 | TCP |
| 3393 | 76.797883 | 192.168.1.155 | 192.168.1.33 | TCP |
| 3394 | 76.797940 | 192.168.1.33 | 192.168.1.155 | TCP |

LAPTOP MAC — IoT MAC

> Frame 3388: 54 bytes on wire (432 bits), 54 bytes captured (432 bits on interface 0
> Ethernet II, Src: ee:e0:b8:45:5c:81 (ee:e0:b8:45:5c:81), Dst: de:ad:b8:7f:fe:11 (de:ad:b8:7f:fe:11)
> Internet Protocol verson 4, Src: 192.168.1.155, Dst: 192.168.1.33
> Transmission Control Protocol, Src Port: 20035, Dst PORT: 80, Seq: 294, Ack: 5, Len: 0

FIG. 7A

| LENGTH | INFO |
|---|---|
| 60 | 80 → 20035 [PSH, ACK] Seq=2 Ack=294 Win=1755 Len=1 [TCP segment of a reassembled PDU] |
| 54 | 20035 → 80 [ACK] Seq=294 Ack=3 Win=65535 Len=0 |
| 60 | 80 → 20035 [PSH, ACK] Seq=3 Ack=294 Win=1755 Len=1 [TCP segment of a reassembled PDU] |
| 54 | 20035 → 80 [ACK] Seq=294 Ack=4 Win=65535 Len=0 |
| 60 | 80 → 20035 [PSH, ACK] Seq=4 Ack=294 Win=1755 Len=1 [TCP segment of a reassembled PDU] |
| 54 | 20035 → 80 [ACK] Seq=294 Ack=5 Win=65535 Len=0 |
| 60 | 80 → 20035 [PSH, ACK] Seq=5 Ack=294 Win=1755 Len=1 [TCP segment of a reassembled PDU] |
| 60 | 80 → 20035 [PSH, ACK] Seq=6 Ack=294 Win=1755 Len=1 [TCP segment of a reassembled PDU] |
| 54 | 20035 → 80 [ACK] Seq=294 Ack=7 Win=65535 Len=0 |
| 60 | 80 → 20035 [PSH, ACK] Seq=7 Ack=294 Win=1755 Len=1 [TCP segment of a reassembled PDU] |
| 54 | 20035 → 80 [ACK] Seq=294 Ack=8 Win=65535 Len=0 |
| 60 | 80 → 20035 [PSH, ACK] Seq=8 Ack=294 Win=1755 Len=1 [TCP segment of a reassembled PDU] |

FIG. 7B

| NO. | TIME | SOURCE | DESTINATION | PROTOCOL | LENGTH | INFO |
|---|---|---|---|---|---|---|
| 25 | 12.782658 | 192.168.1.155 | 204.79.197.222 | TLSv1.2 | 141 | Application Data |
| 26 | 12.782792 | 192.168.1.155 | 204.79.197.222 | TLSv1.2 | 132 | Application Data |
| 28 | 12.800483 | 204.79.197.222 | 192.168.1.155 | TCP | 60 | 443 → 19961 [ACK] Seq=151 Ack=711 Win=261888 Len=0 |
| 29 | 12.800590 | 204.79.197.222 | 192.168.1.155 | TLSv1.2 | 123 | Application Data |
| 30 | 12.800665 | 192.168.1.155 | 204.79.197.222 | TCP | 54 | 19961 → 443 [ACK] Seq=711 Ack=220 Win=261888 Len=0 |
| 31 | 12.801044 | 192.168.1.155 | 204.79.197.222 | TLSv1.2 | 92 | Application Data |
| 32 | 12.805537 | 204.79.197.222 | 192.168.1.155 | TLSv1.2 | 1514 | Application Data |
| 33 | 12.805538 | 204.79.197.222 | 192.168.1.155 | TLSv1.2 | 498 | Application Data |
| 34 | 12.782658 | 204.79.197.222 | 192.168.1.155 | TLSv1.2 | 392 | Application Data |
| 35 | 12.805538 | 204.79.197.222 | 192.168.1.155 | TLSv1.2 | 92 | Application Data |
| 36 | 12.805695 | 192.168.1.155 | 204.79.197.222 | TCP | 54 | 19961 → 443 [ACK] Seq=749 Ack=2500 Win=262144 Len=0 |
| 37 | 12.830724 | 204.79.197.222 | 192.168.1.155 | TCP | 60 | 443 → 19961 [ACK] Seq=2500 Ack=749 Win=26188 Len=0 |

WEBSITE IP ADDRESS / LAPTOP LAN IP ADDRESS

> Frame 32: 1514 bytes on wire (121112 bits), 1514 bytes captured (12112 bits) on interface 0
> Ethernet II, Src: Netrear_d7:6a:b4 (b0:b9:8a:d7:6a:b4), Dst: ee:e0:b8:45:5c:81 (ee:e0:b8:45:5c:81) ← LAPTOP MAC
> Internet Protocol Version 4, Src: 204.79.197.222, Dst: 192.168.1.155
> Transmission Control Protocol, Src Port: 443, Dst PORT: 19961, Seq: 220, Ack: 711, Len: 1460
> Secure Sockets Layer

FIG. 8

```
         SOURCE:   whois.arin.net
     IP ADDRESS:   204.79.197.222
           NAME:   ECN-NETWORK
         HANDLE:   NET-204-79-195-0-1
REGISTRATION DATE: 12/15/94
          RANGE:   204.79.195.0.204  79.107.258
            ORG:   MICROSOFT CORPORATION
     ORG HANDLE:   MSFT
        ADDRESS:   ONE MICROSOFT WAY
           CITY:   REMOND
 STATE/PROVINCE:   WA
    POSTAL CODE:   98052
        COUNTRY:   UNITED STATES
   NAME SERVERS
```

*FIG.9*

SYSTEM AND METHOD FOR MONITORING HEALTH STATUS BASED ON HOME INTERNET TRAFFIC PATTERNS

CROSS-REFERENCE TO PRIOR APPLICATIONS

This application claims the benefit of U.S. Provisional Application No. 62/945,447, filed on 9 Dec. 2019. This application is hereby incorporated by reference herein.

BACKGROUND OF THE INVENTION

1. Field of the Invention

The present invention pertains to system and method for remotely monitoring the health status of individuals, and, in particular, to a system and method for remotely monitoring the health status of individuals based on the analysis of home Internet traffic patterns.

2. Description of the Related Art

Remote health monitoring uses technology to monitor patients in non-clinical environments, such as in the home. Remote health monitoring has the potential to keep people, such as those suffering with chronic diseases, healthy, and to allow older and disabled individuals to live at home longer and avoid having to move into skilled nursing facilities. Remote health monitoring can also serve to reduce the number of hospitalizations, readmissions, and lengths of stay in hospitals—all of which help improve quality of life and contain costs. As a result, remote health monitoring is growing in popularity as a means to significantly improve quality of life and/or contain costs.

There is thus a need for systems and methods that improve the field of remote health monitoring.

SUMMARY OF THE INVENTION

Accordingly, it is an object of the present invention to provide, in one embodiment, a method of monitoring the health status of an occupant of a dwelling based on Internet traffic of the dwelling. The method includes: (a) analyzing transport layer data for the Internet traffic of the dwelling for a period of time to identify a plurality of occupant specific transport layer data items, wherein each occupant specific transport layer data item includes one of a number of occupant specific MAC addresses, wherein each occupant specific transport layer data item is identified based on the one of the number of occupant specific MAC addresses, and wherein each of the number of occupant specific MAC addresses is associated with a device used by the occupant, (b) establishing an Internet traffic pattern for the occupant for the period of time based on the identified plurality of occupant specific transport layer data items, (c) comparing the established Internet traffic pattern to a predetermined baseline Internet traffic pattern for the occupant and identifying a deviation from the predetermined baseline Internet traffic pattern based on the comparison, and (d) determining that a change in the health status is possible for the occupant based on the identifying of the deviation.

In another embodiment, a health status server configured for monitoring the health status of an occupant of a dwelling based on Internet traffic of the dwelling is provided. The health status server comprises a processing apparatus having a processor and a memory, wherein the processing apparatus is structured and configured to: (a) analyze transport layer data for the Internet traffic of the dwelling for a period of time to identify a plurality of occupant specific transport layer data items, wherein each occupant specific transport layer data item includes one of a number of occupant specific MAC addresses, wherein each occupant specific transport layer data item is identified based on the one of the number of occupant specific MAC addresses, and wherein each of the number of occupant specific MAC addresses is associated with a device used by the occupant, (b) establish an Internet traffic pattern for the occupant for the period of time based on the identified plurality of occupant specific transport layer data items, (c) compare the established Internet traffic pattern to a predetermined baseline Internet traffic pattern for the occupant and identifying a deviation from the predetermined baseline Internet traffic pattern based on the comparison, and (d) determine that a change in the health status is possible for the occupant based on the identifying of the deviation.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 7A, 7B and 8 show exemplary connection logs that may be accessed by a health status server according to an exemplary embodiment of the disclosed concept;

FIG. 9 illustrates how a reverse DNS lookup of a WAN IP address can be used to identify a particular website according to an exemplary embodiment of the disclosed concept;

DETAILED DESCRIPTION OF EXEMPLARY EMBODIMENTS

Figure 1:
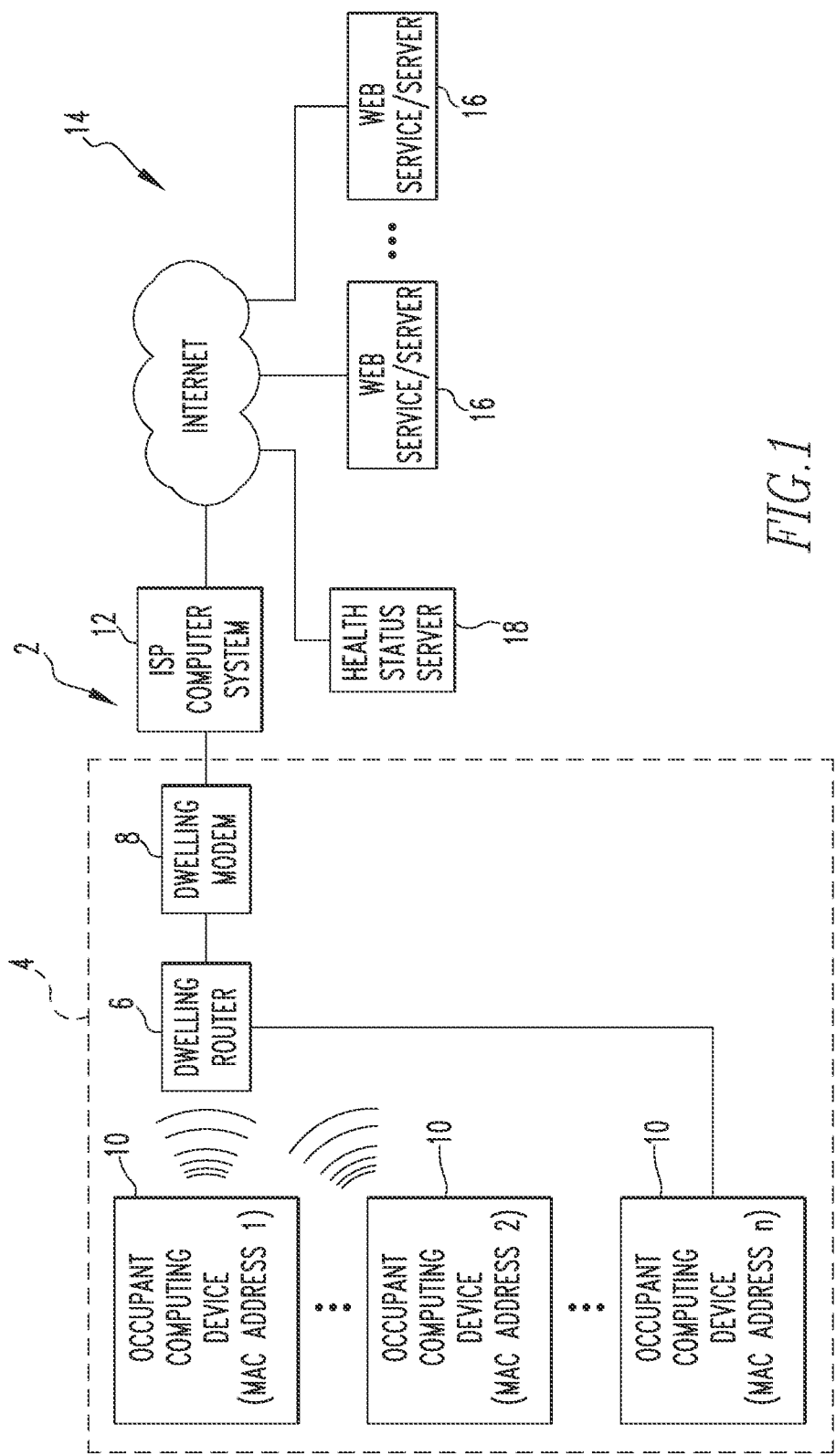
FIG. 1 is a schematic diagram of a system for detecting and monitoring changes in behavior of one or more occupants of a dwelling that could indicate a change in health status of those occupants according to a first exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept relates to a system and method for detecting and monitoring changes in behavior of individuals that could indicate a change in health status of those individuals. More specifically, as described in greater detail herein in connection with various particular embodiments, the system and method of the disclosed concept captures and analyzes the Internet traffic for a dwelling (e.g., a home or an apartment) in order to identify deviations from normal/baseline Internet traffic that would be indicative of a change in behavior for particular occupants of the dwelling that in turn would be indicative of a possible change in health status for those particular occupants. Once such deviations are identified, corrective actions can be taken early on to address health concerns.

More particularly, as is known, the network packets that make up the Internet traffic for a dwelling includes certain unencrypted (i.e., clear text) transport layer data that can be used to identify the source and destination and time of each communication. Specifically, the transport layer data includes: (i) the MAC (media access control) address of the source device, such as a tablet, smartphone or laptop, of the communication in question (e.g., a request to access a certain web service/server), (ii) the IP address of the destination (e.g., web service/server) of the communication in question, and (iii) a timestamp indicating the time of the communication. According to an aspect of the disclosed concept, certain devices in a dwelling are assumed to be associated with a particular occupant of the dwelling. For example, tablets, smartphones and laptops are often single-user devices. Therefore, according to an aspect of the disclosed concept, each MAC address in the dwelling, which is associated with a particular device, is assumed to be associated with a particular occupant of the dwelling. Based on these assumptions, the disclosed concept employs a clear mapping of the MAC address of the dwelling to the occupants of the dwelling, and, as described in greater detail herein, uses that mapping to monitor for Internet traffic behavior changes that could indicate changes in health status.

In addition, and as also described in greater detail herein, the disclosed concept employs a health status server (HSS) to capture and analyze the home Internet traffic to monitor for Internet traffic behavior changes that could indicate changes in health status. In the exemplary embodiment, the HSS is a wide area network (WAN) (e.g., Internet) connected computing device, such as a server computer, operated by a third party service provider.

Furthermore, during a baseline establishment/calibration stage, the HSS will, for each participating dwelling, capture the unencrypted transport layer data for a period of time to establish a baseline Internet traffic pattern for each occupant of the dwelling (i.e., for when the occupant is in a normal, healthy state). For example, the baseline Internet traffic pattern for each occupant may be for a day, but other periods are possible. More specifically, the HSS will analyze the unencrypted transport layer data to determine the associated MAC address so that each item of data can be classified as being associated with a particular occupant of the dwelling. Based thereon, the occupant classified transport layer data collected over time can be used to establish a baseline Internet traffic pattern for each occupant (i.e., for the set of one or more MAC addresses assumed to be associated with the occupant as described above) for a relevant period (e.g., a day). In addition, in one embodiment, to assist with this upfront baseline establishment/calibration stage, the HSS will ask questions of each occupant of a dwelling to establish whether the person is in a healthy/normal status to confirm that the data being used in this stage is in fact associated with a healthy/normal status of the occupant. For example, if a week is needed to establish a baseline, then at the end of the week, questions such as, "were you ill last week?" "if yes, what days?" could be asked of each occupant to ensure proper use of the collected data. Moreover, the baseline for any occupant may change over a longer period of months and years. Thus, in one embodiment, the HSS can track the baseline for each occupant and update it as needed to keep the baseline current and relevant.

Moreover, following the baseline establishment/calibration stage, the HSS will perform ongoing monitoring. During such an ongoing monitoring stage, the HSS will, for each participating dwelling, capture on an ongoing basis the unencrypted transport layer data for the dwelling. The HSS will then analyze the captured transport layer data to identify, for each occupant of the dwelling, deviations from the previously established baseline that would be indicative of behavior changes indicating a possible change in health status. More specifically, during this stage, the HSS will analyze the transport layer data on an ongoing basis to determine the associated MAC address of each item of data so that each item of data can be classified as being associated with a particular occupant. Based thereon, the classified transport layer data will be used by the HSS to establish an Internet traffic pattern for each occupant for the relevant time period (e.g., each day or other chosen period). That pattern is then compared to the baseline for the occupant to identify deviations from baseline that would be indicative of behavior changes indicating a possible change in health status for that occupant.

FIG. 1 is a schematic diagram of a system 2 implemented in connection with a dwelling 4 for detecting and monitoring changes in behavior of one or more occupants of dwelling 4 that could indicate a change in health status of those occupants according to a first exemplary embodiment of the disclosed concept. As seen in FIG. 1, dwelling 4 includes a dwelling router 6 that is operatively coupled to a dwelling modem 8. As is well known, dwelling router 6 is a hardware networking device that forwards data packets between computer networks, and dwelling modem 8 is a hardware device that converts the data into a format suitable for the transmission via the medium in question. In the exemplary embodiment, dwelling router 6 is a wireless router that combines the networking functions of a wireless access point and a router. Dwelling 4 also includes a number of occupant computing devices 10, each with an assigned, unique MAC address. In the exemplary embodiment shown in FIG. 1, dwelling 4 includes n computing devices 10 having MAC addresses 1 through n. As shown in FIG. 1, one or more of occupant computing devices 10 may be provided with wireless (e.g., WiFi) capability for wirelessly communicating with dwelling router 6, while other ones of occupant computing devices 10 may be connected to dwelling router 6 by way of a wired connection. Occupant computing devices 10 may be any of a number of different types of computing devices such as, without limitation, a tablet computer, a smartphone, a laptop computer, a voice assistant device (e.g., an Amazon® Echo® or Alexa® device), or a home security system.

In addition, as also seen in FIG. 1, system 2 further includes an Internet service provider (ISP) computer system 12 that is in operative communication (e.g., wired) with dwelling modem 8. ISP computer system 12 enables each of the occupant computing devices 10 of dwelling 4 to be connected to a WAN 14 (through dwelling router 6 and dwelling modem 8) so that such devices can connect as requested to one or more web services/servers 16 of WAN 14. In the illustrated exemplary embodiment, WAN 14 comprises the Internet.

Figure 2:
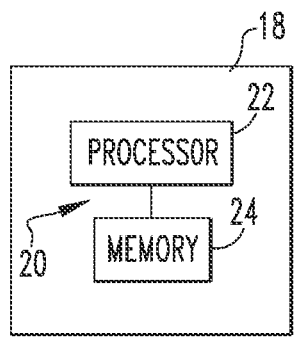
FIG. 2 is a schematic diagram of a health status server (HSS) according to an exemplary embodiment of the disclosed concept.

Moreover, as further seen in FIG. 1, WAN 14 includes a health status server (HSS) 18 for implementing the detecting and monitoring methodology of the disclosed concept as described in detail herein in the various embodiments. In the exemplary embodiment, as seen in FIG. 2, HSS 18 includes a processing apparatus 20 including a processor 22 and a memory 24. Processor 22 may be, for example and without limitation, a microprocessor (µP), a microcontroller, or some other suitable processing device, that interfaces with memory 24 (which may be separate from or included as part of processor 22). Memory 24 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 24 has stored therein a number of routines that are executable by processor 22. One or more of the routines implement (by way of computer/processor executable instructions) a method of capturing and analyzing the Internet traffic for dwelling 4 in order to identify deviations from normal/baseline Internet traffic that would be indicative of a change in behavior for particular occupants of dwelling 4 that in turn would be indicative of a change in health status for those particular occupants according to any of the various embodiments described herein.

Figure 3:
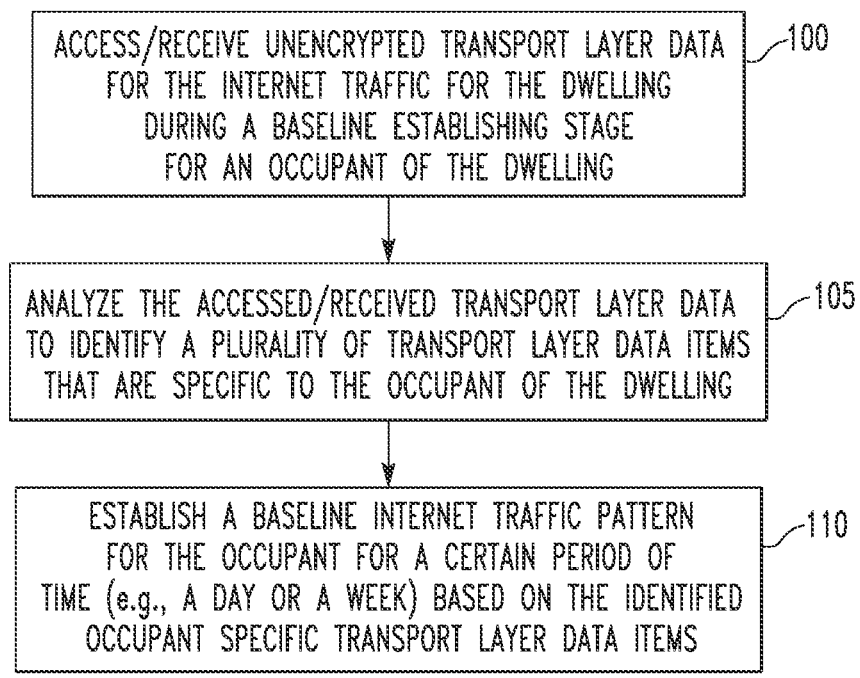
FIG. 3 is a flowchart illustrating a method of establishing a baseline Internet traffic pattern for an occupant of a dwelling according to an exemplary embodiment of the disclosed concept.

FIG. 3 is a flowchart illustrating a method of establishing a baseline Internet traffic pattern for an occupant of dwelling 4 according to an exemplary embodiment of the disclosed concept. The method shown in FIG. 3 may be implemented in HSS 18 shown in FIGS. 1 and 2 by way of a number of routines stored in memory 24 and executable by processor 22 of processing apparatus 20 of HSS 18. As will be appreciated, once the baseline Internet traffic pattern for the occupant is established as shown in FIG. 3, it may then thereafter be used in the disclosed concept (e.g., see FIG. 4 discussed below) to identify Internet traffic pattern deviations that are indicative of a behavior change that may indicate a possible change of health status of the occupant.

Referring to FIG. 3, the method begins at step 100, wherein HSS 18 accesses and receives unencrypted transport layer data for the Internet traffic for dwelling 4 during a baseline establishing/calibration stage. Typically, step 100 will be performed over a predetermined period of time, such as, for example, and without limitation, one or more weeks or months, in order to establish a baseline Internet traffic pattern for an occupant of dwelling 4 for a predetermined period of time, such as a day. In the present exemplary embodiment, HSS 18 accesses and receives unencrypted transport layer data for the Internet traffic for dwelling 4 by periodically querying the connection logs of dwelling router 6. Although not technically required for sending the Internet traffic information to HSS 18, it is preferred to employ a secured connection (e.g., https) to protect privacy. As will be appreciated, in this embodiment, dwelling router 6 is structured and configured to allow for such remote access, which may be by way of a username and password login (provided to HSS 18 by the occupant of dwelling 4). HSS 18 will be able to access dwelling router 6 in this manner by way of the WAN IP address of dwelling router 6, which may be obtained from a domain name server (DNS) or from ISP computer system 12. Alternatively, HSS 18 access and receive the unencrypted transport layer data for the Internet traffic for dwelling 4 by periodically querying the connection logs of ISP computer system 12 using the IP address of dwelling router 6. Depending on the policies of the ISP and if they manage the router, the MAC addresses may or may not be logged. In this embodiment, such access would be by way of an agreement between the Internet service provider, the HSS third party provider and the occupant of dwelling whose traffic is to be analyzed.

Referring again to FIG. 3, the method then proceeds to step 105. At step 105, HSS 18 analyzes the accessed and received transport layer data to identify a plurality of transport layer data items that are specific to the occupant in question. As discussed elsewhere herein, occupant specific transport layer data items are identified by way of the previously discussed mapping of MAC addresses of occupant computing devices 10 to particular occupants of dwelling 4. More specifically, HSS 18 will analyze the received transport layer data to determine the associated MAC address so that each item of data can be classified as being associated with a particular occupant. Next, at step 110, the transport layer data collected over time that is determined to be associated with the one or more MAC addresses of the particular occupant in question will be used to establish a baseline Internet traffic pattern for the occupant for a relevant period (e.g., a day).

Figure 4:
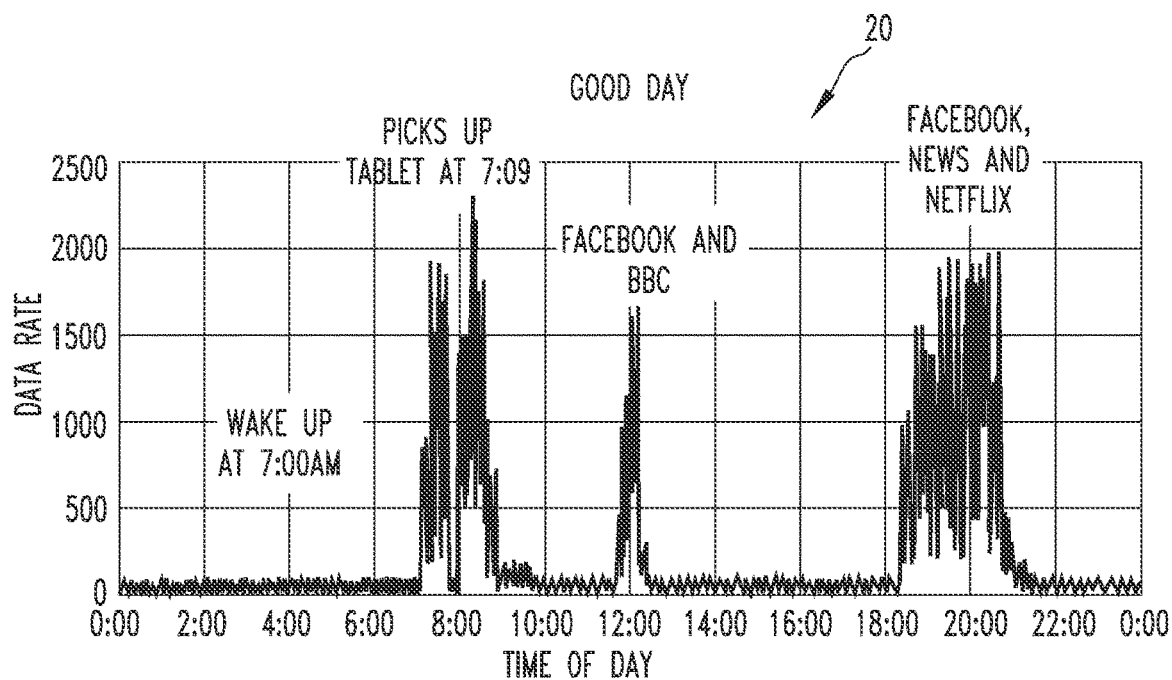
FIG. 4 shows an exemplary baseline Internet traffic pattern for a typical "good day" according to an exemplary embodiment of the disclosed concept.

An exemplary baseline Internet traffic pattern 20 for a typical "good day" is shown in FIG. 4. As seen in FIG. 4, the exemplary baseline Internet traffic pattern 20 comprises information regarding "normal" data usage rates versus time for the occupant for the relevant period. As will be appreciated, low data rates generally imply that there is little human initiated Internet activity during that interval. Thus, in the example shown FIG. 4, which is a baseline normal or healthy day, data rates are low before 7 AM, between 9 AM and noon, and between 1 PM and 6 PM.

Figure 5:
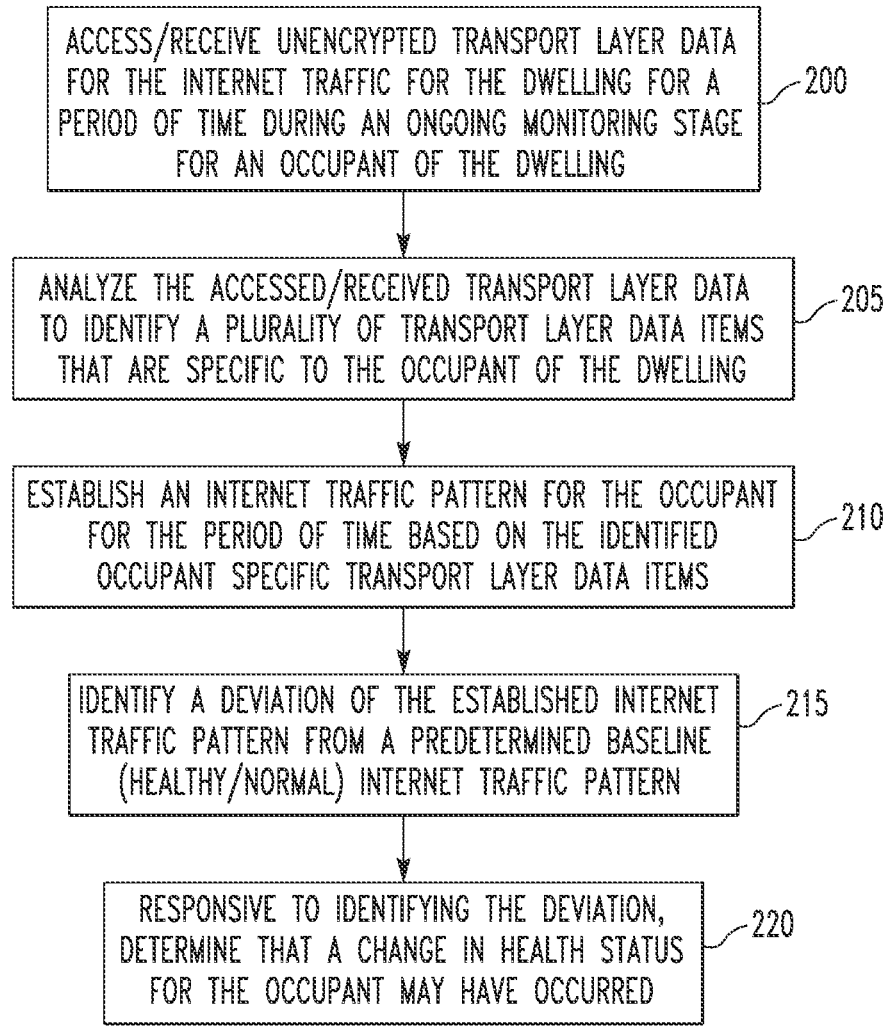
FIG. 5 is a flowchart illustrating a method of capturing and analyzing Internet traffic data to identify Internet traffic pattern deviations that are indicative of a behavior change that may indicate a possible change of health status of an occupant of dwelling according to an exemplary embodiment of the disclosed concept.

FIG. 5 is a flowchart illustrating a method of capturing and analyzing Internet traffic data to identify Internet traffic pattern deviations that are indicative of a behavior change that may indicate a possible change of health status of an occupant of dwelling 4 according to an exemplary embodiment of the disclosed concept. The method shown in FIG. 5 may be implemented in HSS 18 shown in FIG. 1 by way of a number of routines stored in memory 24 and executable by processor 22 of processing apparatus 20 of HSS 18. As discussed below, the method shown in FIG. 5 uses the baseline Internet traffic pattern for the particular occupant in question that was established by way of the method of FIG. 3.

Referring to FIG. 5, the method begins at step 200, wherein HSS 18 accesses and receives unencrypted transport layer data for the Internet traffic for dwelling 4 for a period of time. As discussed elsewhere herein in connection with FIG. 3, HSS 18 may, in this embodiment, access and receive the unencrypted transport layer data by accessing the connection logs of dwelling router 6 or, alternatively, by accessing the connection logs of ISP computer system 12. Next, at step 205, HSS 18 analyzes the accessed and received transport layer data to identify a plurality of transport layer data items that are specific to the occupant of the dwelling. As discussed elsewhere herein, occupant specific transport layer data items may be identified in step 205 way of the previously discussed mapping of MAC addresses of occupant computing devices 10 to particular occupants of dwelling 4. Then, at step 210, HSS 18 will establish an Internet traffic pattern for the occupant in question for the relevant time period based on the identified occupant specific transport layer data items.

Figure 6:
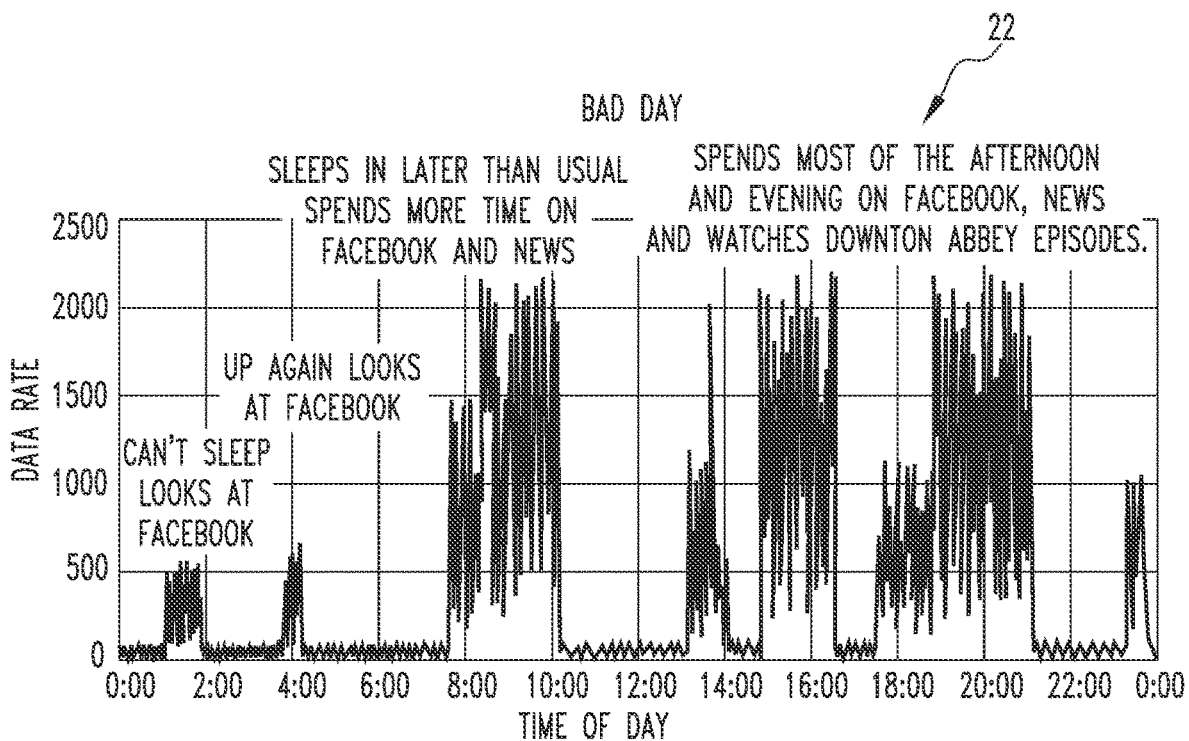
FIG. 6 shows an exemplary Internet traffic pattern established in the method of FIG. 5.

FIG. 6 is an exemplary Internet traffic pattern 22 established in step 210 of FIG. 5. The exemplary Internet traffic pattern 22 shown in FIG. 6 is for an exemplary "bad day" and represents behavior that may indicate a change in health status for the occupant. As seen in FIG. 6, Internet traffic pattern 22 shows increased data rates during the late night and early morning hours resulting from not being able to fall asleep and from late device usage. In addition, sleeping in beyond the normal wake-up time would push Internet usage to a later time. Thus, Internet traffic pattern 22 presents a substantial deviation from exemplary normal Internet traffic pattern 20 shown in FIG. 5.

Following step 210, the method proceeds to step 215, wherein HSS 18 will identify a deviation of the Internet traffic pattern established in step 210 from the predetermined baseline Internet traffic pattern that was determined in FIG. 3. Then, at step 220, responsive to identifying such a deviation, HSS 18 will determine that a change in health status for the occupant may have occurred based on this change in behavior In one embodiment, a health care provider of the occupant would be alerted by HSS 18 and as a minimum would monitor more closely the health status of the occupant. In cases where the behavior is extreme, such as being up all night or many times during the night, the health care provider would likely contact the home of the occupant to gather further information and context. Given the longitudinal information gathered by this system, appropriate and important changes in the care plan are also contemplated. Furthermore, an artificial intelligence (AI) system could be employed as part of HSS 18 to analyze the received data in order to make a more detailed diagnosis. The health care provider may be a professional such as a nurse, physician, licensed practitioner, volunteer, family member or friend.

FIGS. 7A, 7B and 8 show exemplary connection logs 24 and 26 that may be accessed by HSS 18 and that provides the MAC address information that is needed for the methods of FIGS. 3 and 5. As seen in FIGS. 7A and 7B, this exemplary connection log 24 shows Wi-Fi traffic between an exemplary laptop and Internet of things (IoT) device. In this example, the laptop was assigned a Local Area Network (LAN) address of 192.168.1.155, but this can change when the laptop goes offline and another device is assigned that address. The MAC address (ee:e0:b8:45:5c:81), however, is unique and permanently associated with the laptop. As seen in FIG. 8, this exemplary connection log 24 shows Wi-Fi traffic between the exemplary laptop and a website. As seen, even if the laptop LAN has changed, the MAC address will remain the same. FIG. 9 illustrates how a reverse DNS lookup of the WAN IP address can be used to identify the particular website the accessed.

Figure 10:
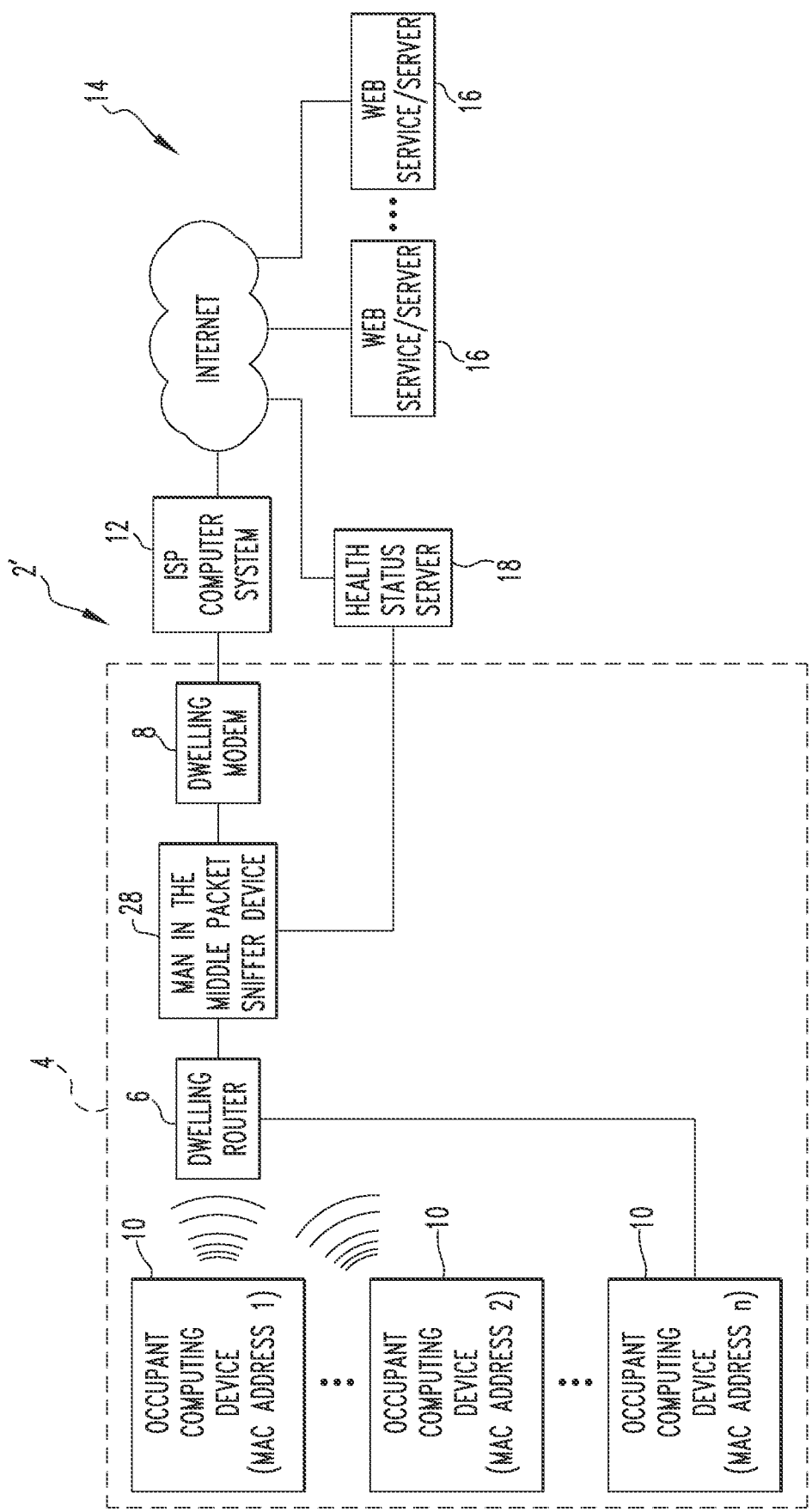
FIG. 10 is a schematic diagram of a system for detecting and monitoring changes in behavior of one or more occupants of a dwelling that could indicate a change in health status of those occupants according to a second, alternative exemplary embodiment of the disclosed concept.

FIG. 10 is a schematic diagram of a system 2' implemented in connection with dwelling 4 for detecting and monitoring changes in behavior of one or more occupants of dwelling 4 that could indicate a change in health status of those occupants according to a second, alternative exemplary embodiment of the disclosed concept. System 2' is similar to system 2, and like components are labeled with like reference numerals. However, system 2' provides an alternative mechanism for accessing and receiving transport layer data for the Internet traffic for dwelling 4 (e.g., steps 100 in FIGS. 3 and 200 and FIG. 5). Specifically, system 2' includes a man-in-the-middle packet sniffer device 28 that is provided between dwelling router 6 and dwelling modem 8. Man-in-the-middle packet sniffer device 28 is a computing device that is structured and configured to have access to the Internet traffic data passing between dwelling router 6 and dwelling modem 8 and to be able to transmit that information (e.g. wirelessly by way of a Wi-Fi broadband connection or by way of a wired (e.g. Ethernet cable) connection) to HSS 18. In the exemplary embodiment, the transport layer of that traffic would be analyzed by man-in-the-middle packet sniffer device 28, and some or all of the traffic information would then be sent to HSS 18. In the exemplary embodiment, dwelling router 6 is configured to be connected to dwelling modem 8 by way of an Ethernet connection, and man-in-the-middle packet sniffer device 28 would make its connection by way of that Ethernet path.

Figure 11:
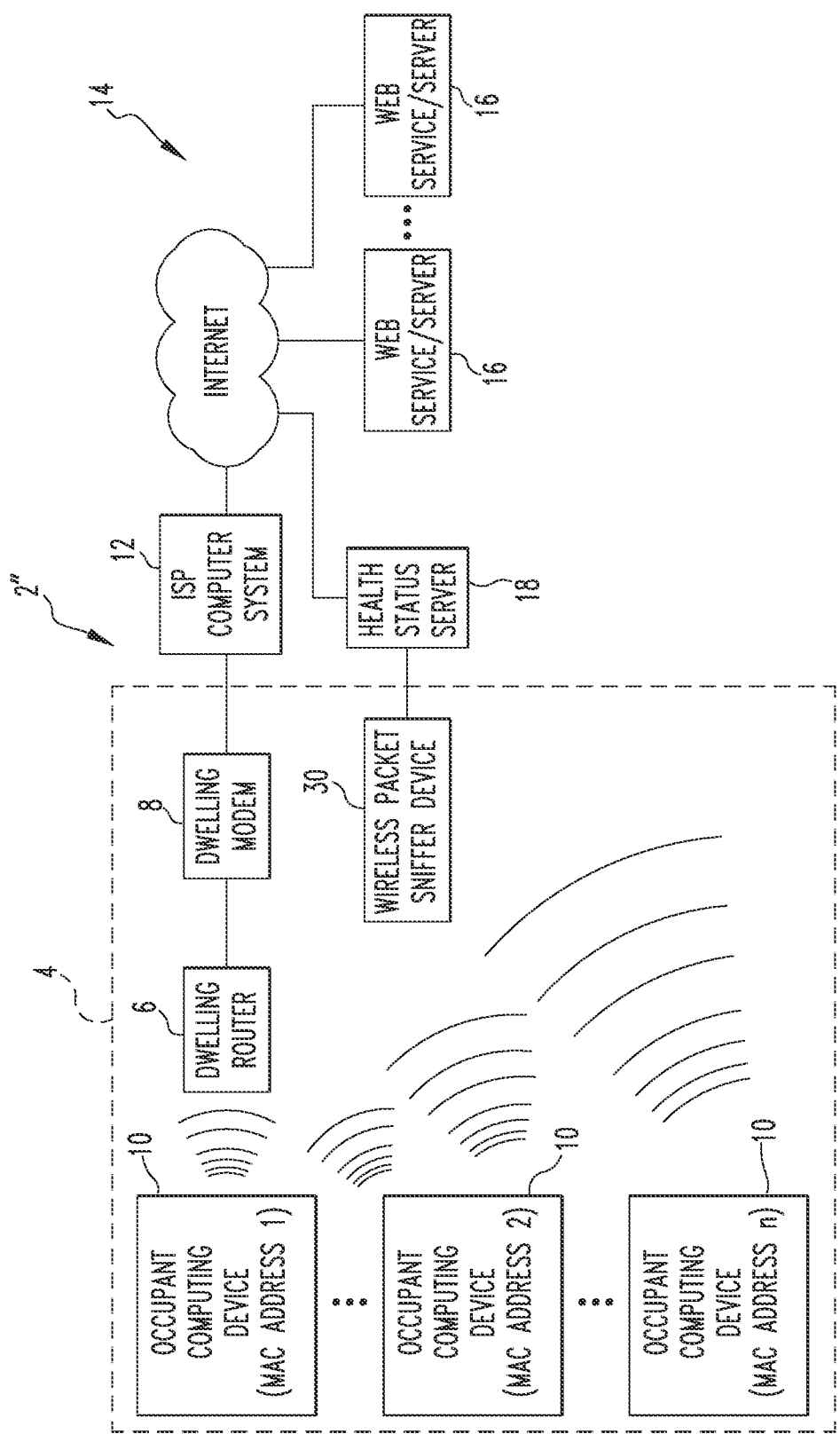
FIG. 11 is a schematic diagram of a system for detecting and monitoring changes in behavior of one or more occupants of a dwelling that could indicate a change in health status of those occupants according to a third, alternative exemplary embodiment of the disclosed concept.

FIG. 11 is a schematic diagram of a system 2" implemented in connection with dwelling 4 for detecting and monitoring changes in behavior of one or more occupants of dwelling 4 that could indicate a change in health status of those occupants according to a third, alternative exemplary embodiment of the disclosed concept. System 2" is similar to system 2, and like components are labeled with like reference numerals. However, system 2" provides a further alternative mechanism for accessing and receiving transport layer data for the Internet traffic for dwelling 4 (e.g., steps 100 in FIGS. 3 and 200 and FIG. 5). Specifically, system 2" includes a wireless packet sniffer device 30 that is structured and configured to have wireless access to the Internet traffic data passing between the devices 10 and the dwelling router 6 and to be able to transmit that information (e.g., wirelessly by way of a Wi-Fi or broadband connection or by way of a wired (e.g. Ethernet cable) connection) to HSS 18. Wireless packet sniffer device 30 may be a dedicated hardware device, or may be a computing device such as a laptop or smartphone that is configured with Wi-Fi packet sniffer software. In the exemplary embodiment, the transport layer of that traffic would be analyzed by wireless packet sniffer device 30, and some or all of the traffic information would then be sent to HSS 18.

In a further alternative embodiment, HSS 18 is configured to monitor the Internet traffic data for the dwelling to determine whether an occupant has a health related Internet service (such as WebMD®). In this embodiment, HSS 18 will determine that a possible change in the health status has occurred for the occupant based on both the identification of the deviation and based on the fact that the occupant has accessed the health related Internet service.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring a health status of an occupant of a dwelling based on Internet traffic of the dwelling, comprising:
    establishing and storing, during a baseline establishment/calibration stage, a predetermined baseline Internet traffic pattern for the occupant for a specific relevant period based on baseline Internet traffic data of the dwelling for the occupant, wherein the baseline Internet traffic pattern for the occupant is determined using a plurality of baseline occupant specific transport layer data items, wherein each baseline occupant specific transport layer data item includes one of a number of occupant specific MAC addresses, wherein each of the number of occupant specific MAC addresses is associated with a device used by the occupant, and wherein the plurality of baseline occupant specific transport layer data items are identified based on the number of occupant specific MAC addresses;
    subsequent to the baseline establishment/calibration stage, analyzing transport layer data for the Internet traffic of the dwelling for a period of time that corresponds to and matches the specific relevant period to identify a plurality of occupant specific transport layer data items, wherein each occupant specific transport layer data item includes one of the number of occupant specific MAC addresses, wherein each occupant specific transport layer data item is identified based on the one of the number of occupant specific MAC addresses;
    establishing an Internet traffic pattern for the occupant for the period of time based on the identified plurality of occupant specific transport layer data items;
    comparing the established Internet traffic pattern to a predetermined baseline Internet traffic pattern for the occupant and identifying a deviation from the predetermined baseline Internet traffic pattern based on the comparison; and
    determining that a change in the health status is possible for the occupant based on the identifying of the deviation.

2. The method according to claim 1, wherein the Internet traffic pattern for the occupant for the period of time comprises first information indicative of data usage rates versus time for the occupant for the period of time, and wherein the baseline Internet traffic pattern comprises second information indicative of baseline data usage rates versus time.

3. The method according to claim 1, wherein the Internet traffic pattern for the occupant for the period of time comprises first information indicative of particular Internet services accessed versus time for the occupant for the period of time, and wherein the baseline Internet traffic pattern comprises second information indicative of baseline Internet services accessed versus time.

4. The method according to claim 1, wherein the period of time is a day or a week or a month.

5. The method according to claim 1, further comprising determining that the occupant has accessed one of a particular number of predetermined health related Internet services during the period of time, wherein the determining that the change in the health status is possible for the occupant is based on the identifying of the deviation and on the determining that the occupant has accessed the one of the particular number of predetermined health related Internet services during the period of time.

6. The method according to claim 1, wherein the analyzing, establishing, comparing and determining steps are performed by a health status server located remote form the dwelling.

7. The method according to claim 6, further comprising receiving the transport layer data for the Internet traffic of the dwelling for the period of time in the health status server from a packet sniffer device located in the dwelling.

8. The method according to claim 7, wherein the packet sniffer device located in the dwelling is a man in the middle device packet sniffer device wired between a router in the dwelling and a modem in the dwelling.

9. The method according to claim 7, wherein the packet sniffer device located in the dwelling is a wireless packet sniffer device located in the dwelling.

10. The method according to claim 6, wherein the health status server accesses the transport layer data for the Internet traffic of the dwelling for the period of time by accessing router connection logs of a router in the dwelling.

11. The method according to claim 6, wherein the health status server accesses the transport layer data for the Internet traffic of the dwelling for the period of time by accessing connection logs associated with the dwelling of an Internet service provider for the dwelling.

12. A health status server configured for monitoring a health status of an occupant of a dwelling based on Internet traffic of the dwelling, comprising:
    a processing apparatus having a processor and a memory, wherein the processing apparatus is structured and configured to:
        establish and store, during a baseline establishment/calibration stage, a predetermined baseline Internet traffic pattern for the occupant for a specific relevant period based on baseline Internet traffic data of the dwelling for the occupant, wherein the baseline Internet traffic pattern for the occupant is determined using a plurality of baseline occupant specific transport layer data items, wherein each baseline occupant specific transport layer data item includes one of a number of occupant specific MAC addresses, wherein each of the number of occupant specific MAC addresses is associated with a device used by the occupant, and wherein the plurality of baseline occupant specific transport layer data items are identified based on the number of occupant specific MAC addresses;

subsequent to the baseline establishment/calibration stage, analyze transport layer data for the Internet traffic of the dwelling for a period of time that corresponds to and matches the specific relevant period to identify a plurality of occupant specific transport layer data items, wherein each occupant specific transport layer data item includes one of the number of occupant specific MAC addresses, wherein each occupant specific transport layer data item is identified based on the one of the number of occupant specific MAC addresses;

establish an Internet traffic pattern for the occupant for the period of time based on the identified plurality of occupant specific transport layer data items;

compare the established Internet traffic pattern to a predetermined baseline Internet traffic pattern for the occupant and identifying a deviation from the predetermined baseline Internet traffic pattern based on the comparison; and determine that a change in the health status is possible for the occupant based on the identifying of the deviation.

13. The health status server according to claim 12, wherein the Internet traffic pattern for the occupant for the period of time comprises first information indicative of data usage rates versus time for the occupant for the period of time, and wherein the baseline Internet traffic pattern comprises second information indicative of baseline data usage rates versus time.

14. The health status server according to claim 12, wherein the Internet traffic pattern for the occupant for the period of time comprises first information indicative of particular Internet services accessed versus time for the occupant for the period of time, and wherein the baseline Internet traffic pattern comprises second information indicative of baseline Internet services accessed versus time.

15. The health status server according to claim 12, wherein the health status server is structured and configured to accesses the transport layer data for the Internet traffic of the dwelling for the period of time by accessing router connection logs of a router in the dwelling.

16. The method according to claim 12, wherein the health status server is structured and configured to accesses the transport layer data for the Internet traffic of the dwelling for the period of time by accessing connection logs associated with the dwelling of an Internet service provider for the dwelling.

17. A computer program product, comprising a non-transitory computer usable medium having a computer readable program code embodied therein, the computer readable program code being adapted and configured to be executed to implement a method of monitoring a health status as recited in claim 1.

* * * * *